US00PP30741P2

(12) United States Plant Patent
Yamada

(10) Patent No.: US PP30,741 P2
(45) Date of Patent: Jul. 23, 2019

(54) ***CATHARANTHUS* PLANT NAMED 'SUNCATFE 291'**

(50) Latin Name: *Catharanthus roseus*
Varietal Denomination: Suncatfe 291

(71) Applicant: Masahiro Yamada, Shiga (JP)

(72) Inventor: Masahiro Yamada, Shiga (JP)

(73) Assignee: Suntory Flowers Limited, Tokyo (JP)

( * ) Notice: Subject to any disclaimer, the term of this patent is extended or adjusted under 35 U.S.C. 154(b) by 0 days.

(21) Appl. No.: 15/732,926

(22) Filed: Jan. 12, 2018

(51) Int. Cl.
*A01H 5/02* (2018.01)

(52) U.S. Cl.
USPC ..... Plt./263.1
CPC ..... *A01H 5/02* (2013.01)

(58) Field of Classification Search
USPC ..... Plt./263.1
See application file for complete search history.

*Primary Examiner* — Anne Marie Grunberg
(74) *Attorney, Agent, or Firm* — C. A. Whealy

(57) ABSTRACT

A new and distinct cultivar of *Catharanthus* plant named 'Suncatfe 291', characterized by its compact, semi-upright and uniformly mounding plant habit; vigorous growth habit; freely basal branching habit; freely flowering habit; long flowering period; relatively small star-shaped light red purple-colored flowers with dark red purple-colored centers; and good garden performance.

1 Drawing Sheet

Botanical designation: *Catharanthus roseus.*
Cultivar denomination: 'SUNCATFE 291'.

BACKGROUND OF THE INVENTION

The present invention relates to a new and distinct *Catharanthus* plant, botanically known as *Catharanthus roseus* and hereinafter referred to by the cultivar name 'Suncatfe 291'.

The new *Catharanthus* plant is a product of a planned breeding program conducted by the Inventor in Higashiomi, Shiga, Japan. The objective of the breeding program is to develop new compact and freely branching *Catharanthus* plants with numerous small attractive flowers.

The new *Catharanthus* plant originated from a cross-pollination conducted by the Inventor in Higashiomi, Shiga, Japan in September, 2013 of a proprietary selection of *Catharanthus roseus* identified as code designation FS8239, not patented, as the female, or seed, parent with a proprietary selection of *Catharanthus roseus* identified as code designation VP8507, not patented, as the male, or pollen, parent. The new *Catharanthus* plant was discovered and selected by the Inventor as a single flowering plant from within the progeny of the stated cross-pollination in a controlled greenhouse environment in Higashiomi, Shiga, Japan in September, 2015.

Asexual reproduction of the new *Catharanthus* plant by vegetative tip cuttings in a controlled greenhouse environment in Higashiomi, Shiga, Japan since December, 2015, has shown that the unique features of this new *Catharanthus* plant are stable and reproduced true to type in successive generations.

SUMMARY OF THE INVENTION

Plants of the new *Catharanthus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Suncatfe 291'. These characteristics in combination distinguish 'Suncatfe 291' as a new and distinct *Catharanthus* plant:

1. Compact, semi-upright and uniformly mounding plant habit.
2. Vigorous growth habit.
3. Freely basal branching habit.
4. Freely flowering habit.
5. Long flowering period.
6. Relatively small star-shaped light red purple-colored flowers with dark red purple-colored centers.
7. Good garden performance.

Plants of the new *Catharanthus* can be compared to plants of the female parent selection. Plants of the new *Catharanthus* differ primarily from plants of the female parent selection in flower color as plants of the female parent selection have light pink-colored flowers.

Plants of the new *Catharanthus* can be compared to plants of the male parent selection. Plants of the new *Catharanthus* differ primarily from plants of the male parent selection in the following characteristics:

1. Plants of the new *Catharanthus* have smaller flowers than plants of the male parent selection.
2. Plants of the new *Catharanthus* and the male parent selection differ in flower color as plants of the male parent selection have light purple-colored flowers.

Plants of the new *Catharanthus* can be compared to plants of the *Catharanthus roseus* 'Suncatha 2439', disclosed in U.S. Plant Pat. No. 27,477. In side-by-side comparisons, plants of the new *Catharanthus* differ from plants of 'Suncatha 2439' in the following characteristics:

1. Plants of the new *Catharanthus* are shorter and narrower than plants of 'Suncatha 2439'.

2. Plants of the new *Catharanthus* have thicker stems than plants of 'Suncatha 2439'.
3. Plants of the new *Catharanthus* and 'Suncatha 2439' differ in flower color as plants of 'Suncatha 2439' have flowers that are dark red purple in color.

BRIEF DESCRIPTION OF THE PHOTOGRAPHS

The accompanying colored photographs illustrate the overall appearance of the new *Catharanthus* plant showing the colors as true as it is reasonably possible to obtain in colored reproductions of this type. Colors in the photographs may differ slightly from the color values cited in the detailed botanical description which accurately describe the colors of the new *Catharanthus* plant.

The photograph at the top of the sheet is a side perspective view of a typical flowering plant of 'Suncatfe 291' grown in a container.

The photograph at the bottom of the sheet is a close-up view of a typical flowering plant of 'Suncatfe 291'.

DETAILED BOTANICAL DESCRIPTION

The aforementioned photographs and following observations, measurements and values describe plants grown during the late summer and early autumn in 20-cm containers in an outdoor nursery in Higashiomi, Shiga, Japan and under cultural practices typical of commercial production. During the production of the plants, day temperatures averaged 25° C. and night temperatures averaged 15° C. Plants were four months old when the photographs were taken and five months old when the description was taken. In the following description, color references are made to The Royal Horticultural Society Colour Chart, 2015 Edition, except where general terms of ordinary dictionary significance are used.

Botanical classification: *Catharanthus roseus* 'Suncatfe 291'.

Parentage:

*Female, or seed, parent*.—Proprietary selection of *Catharanthus roseus* identified as code designation FS8239, not patented.

*Male, or pollen, parent*.—Proprietary selection of *Catharanthus roseus* identified as code designation VP8507, not patented.

Propagation:

*Type*.—By vegetative tip cuttings.

*Time to initiate roots, summer*.—About two weeks at temperatures about 30° C.

*Time to initiate roots, winter*.—About three weeks at temperatures about 25° C.

*Time to produce a rooted young plant, summer*.—About five weeks at temperatures about 30° C.

*Time to produce a rooted young plant, winter*.—About six weeks at temperatures about 25° C.

*Root description*.—Fibrous; typically white in color, actual color of the roots is dependent on substrate composition, water quality, fertilizer type and formulation, substrate temperature and physiological age of roots.

*Rooting habit*.—Freely branching; medium density.

Plant description:

*Plant and growth habit*.—Compact, semi-upright and uniformly mounding plant habit; freely basal branching habit with numerous basal and secondary branches developing per plant; vigorous growth habit.

*Plant height*.—About 18 cm.

*Plant diameter*.—About 32 cm.

Lateral branch description:

*Length*.—About 23 cm.

*Diameter*.—About 4.8 mm.

*Internode length*.—About 8 mm.

*Strength*.—Strong.

*Aspect*.—Upright to outwardly.

*Texture*.—Smooth, glabrous.

*Color*.—Close to 145D tinged with close to 60D.

Leaf description:

*Quantity and arrangement*.—About 18 per lateral branch; opposite, simple.

*Length*.—About 2.6 cm.

*Width*.—About 1.25 cm.

*Shape*.—Elliptical.

*Apex*.—Acute.

*Base*.—Rounded.

*Margin*.—Entire.

*Texture and luster, upper and lower surfaces*.—Smooth, glabrous; glossy.

*Venation pattern*.—Pinnate; reticulate.

*Color*.—Developing leaves, upper surface: Close to 137A. Developing leaves, lower surface: Close to 146A. Fully expanded leaves, upper surface: Close to NN137B; venation, close to 145C. Fully expanded leaves, lower surface: Close to 138A; venation, close to 145D.

*Petioles*.—Length: About 5.2 mm. Diameter: About 1.1 mm. Texture, upper and lower surfaces: Pubescent. Color, upper and lower surfaces: Close to 145C tinged with close to 59D.

Flower description:

*Flower arrangement and habit*.—Single star-shaped salverform flowers arising from upper leaf axils; freely flowering habit with more than 200 to 250 small flowers developing per plant; flowers face mostly upright.

*Fragrance*.—None detected.

*Flowering habit*.—Plants begin flowering about two to three weeks after planting; long flowering period, in the garden, plants flower continuously from the early summer to late autumn in Japan.

*Flower longevity*.—Individual flowers last about two to three days on the plant; flowers not persistent.

*Flower buds*.—Length: About 2.4 cm. Diameter: About 2.5 mm. Shape: Narrowly ovoid with cylindrical tube. Color: Towards the base, close to 145C tinged with close to 35D; mid-section, close to 145B; towards the apex, close to NN155B.

*Flower diameter*.—About 2.2 cm.

*Flower length (depth)*.—About 2.2 cm.

*Tube length*.—About 1.9 cm.

*Tube diameter, proximally*.—About 1 mm.

*Tube diameter, distally*.—About 1.5 mm.

*Corolla*.—Arrangement: Five petals in a single whorl fused at the base into a tube. Petal length from throat: About 1.2 cm. Petal width: About 4.3 mm. Petal shape: Narrowly elliptic to oblanceolate. Petal apex: Acute. Petal margin: Entire. Petal texture, upper and lower surfaces: Smooth, glabrous. Throat texture: Smooth, glabrous. Tube texture: Smooth, glabrous. Color: Petal, when opening, upper surface: Close to 75B; eye, close to 59A. Petal, when opening, lower surface: Close to N155B. Petal, fully opened, upper surface: Close to N74D; towards the base, close to 66B; eye, close to 59B; color does not change with development. Petal, fully opened, lower surface: Close to N155B; towards the apex, close to N74D; color does not change with development. Throat: Proximally, close to 145D; distally, close to 145C. Tube: Proximally, close to 145C tinged with close to 35D; distally, close to 145B.

*Calyx*.—Arrangement: Star-shaped tubular calyx with five sepals fused towards the base. Length: About 1.4 mm. Diameter: About 1.6 mm. Sepal length: About 1.4 mm. Sepal width: About 0.4 mm. Sepal shape: Lanceolate. Sepal apex: Acuminate. Sepal margin: Entire. Sepal texture, upper and lower surfaces: Smooth, glabrous. Color, upper and lower surfaces: Close to 144C.

*Peduncles*.—Length: About 2 mm. Diameter: About 0.9 mm. Angle: Mostly upright. Strength: Strong. Texture: Smooth, glabrous. Color: Close to 145C.

*Reproductive organs*.—Stamens: Quantity per flower: Five. Anther size: About 1.3 mm by 0.6 mm. Anther shape: Narrowly elliptic. Anther color: Close to 11D. Pollen amount: Scarce. Pollen color: Close to 11D. Pistils: Quantity per flower: One. Pistil length: About 1.5 cm. Style color: Close to 157D. Stigma shape: Globose. Stigma color: Close to 144B. Ovary color: Close to 144B. Seeds and fruits: Seed and fruit development have not been observed on plants of the new *Catharanthus* to date.

Garden performance: Plants of the new *Catharanthus* have been observed to have good garden performance and to tolerate wind, rain and temperatures ranging from about 5° C. to about 35° C. to 40° C.

Pathogen & pest resistance: Plants of the new *Catharanthus* have not been observed to be resistant to pathogens and pests common to *Catharanthus* plants to date.

It is claimed:

1. A new and distinct *Catharanthus* plant named 'Suncatfe 291' as illustrated and described.

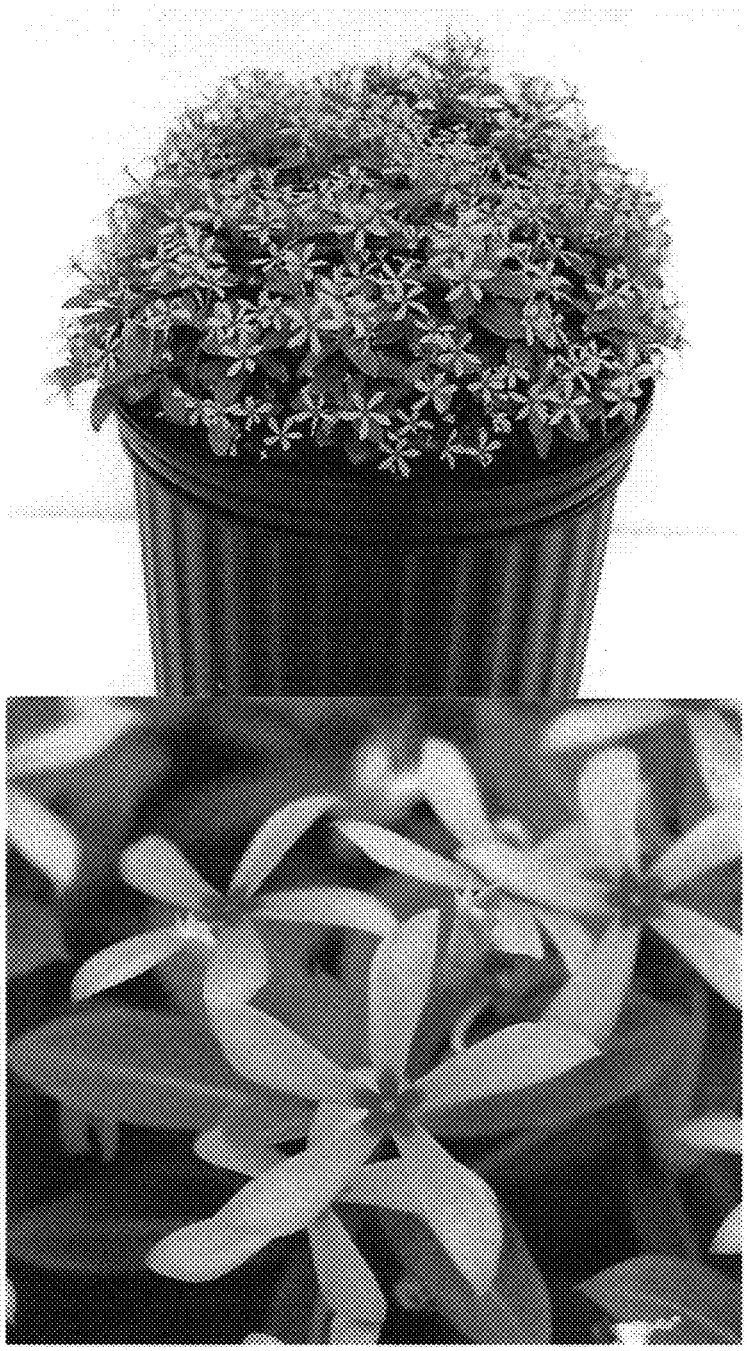

* * * * *